United States Patent
Shuto et al.

(10) Patent No.: US 11,033,511 B2
(45) Date of Patent: Jun. 15, 2021

(54) PHARMACEUTICAL PATCH

(71) Applicant: HISAMITSU PHARMACEUTICAL CO., INC., Tosu (JP)

(72) Inventors: Akira Shuto, Tokyo (JP); Takao Kurokawa, Tsukuba (JP); Junya Horiuchi, Tsukuba (JP); Hidekazu Kuma, Tsukuba (JP); Satoshi Amano, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

(21) Appl. No.: 16/610,955

(22) PCT Filed: Jul. 30, 2018

(86) PCT No.: PCT/JP2018/028460
§ 371 (c)(1),
(2) Date: Nov. 5, 2019

(87) PCT Pub. No.: WO2019/026844
PCT Pub. Date: Feb. 7, 2019

(65) Prior Publication Data
US 2020/0069603 A1 Mar. 5, 2020

(30) Foreign Application Priority Data
Aug. 1, 2017 (JP) .............................. JP2017-149304

(51) Int. Cl.
*A61K 9/70* (2006.01)
*A61K 31/216* (2006.01)

(52) U.S. Cl.
CPC .......... *A61K 9/7061* (2013.01); *A61K 31/216* (2013.01)

(58) Field of Classification Search
CPC .... A61K 9/7061; A61K 31/216; A61K 47/02; A61K 47/06; A61K 9/7053; A61P 13/10
See application file for complete search history.

(56) References Cited

U.S. PATENT DOCUMENTS

| | | | | |
|---|---|---|---|---|
| 5,891,920 A | * | 4/1999 | Hirano | A61K 9/7053 514/629 |
| 2004/0018241 A1 | * | 1/2004 | Houze | A61K 9/0014 424/486 |

FOREIGN PATENT DOCUMENTS

| | | |
|---|---|---|
| EP | 1800671 A1 | 6/2007 |
| EP | 2772252 A1 | 9/2014 |
| JP | H853354 A | 2/1996 |
| JP | 3184534 B2 | 4/2001 |
| JP | 2001517493 A | 10/2001 |
| JP | 200483519 A | 3/2004 |
| JP | 2009520741 A | 5/2009 |
| JP | 201382720 A | 5/2013 |
| JP | 2014125466 A | 7/2014 |
| KR | 100209469 B1 | 7/1999 |
| TW | 201328729 A | 7/2013 |
| WO | 9915210 A2 | 4/1999 |
| WO | 0107018 A1 | 2/2001 |
| WO | 02069942 A1 | 9/2002 |
| WO | 2004019930 A1 | 3/2004 |
| WO | 2007077029 A1 | 7/2007 |
| WO | 2013061969 A1 | 5/2013 |

OTHER PUBLICATIONS

International Search Report dated Oct. 23, 2018 corresponding to application No. PCT/JP2018/028460.
Japanese Notice of Allowance dated Jul. 21, 2020 corresponding to Patent Application No. P2018-567314.
Notice of Allowance dated Aug. 27, 2020 corresponding to Taiwanese application No. 107126464.
Notice of Allowanced dated Dec. 4, 2020 corresponding to Korean Patent Application No. 10-2019-7036116.
Lobo Filho, J., et al. "Clinical Trial of Diflucortolone Valerate in Inflammatory Skin Diseases"; Database Embase Online; 1976.
Search Report dated Apr. 23, 2021 corresponding to European Application No. 18841780.2.

* cited by examiner

*Primary Examiner* — Aradhana Sasan
*Assistant Examiner* — Quanglong N Truong
(74) *Attorney, Agent, or Firm* — Nath, Goldberg & Meyer; Joshua B. Goldberg

(57) ABSTRACT

The present invention provides a patch comprising a backing, and an adhesive layer on the backing, wherein the adhesive layer contains at least one drug selected from the group consisting of oxybutynin and a pharmaceutically acceptable salt thereof, a pressure-sensitive adhesive base, and diflucortolone valerate, and the content of the diflucortolone valerate is 0.0007 to 0.05% by mass based on the total mass of the adhesive layer.

3 Claims, No Drawings

PHARMACEUTICAL PATCH

This is a National Phase Application filed under 35 U.S.C. 371 as a national stage of PCT/JP2018/028460, filed Jul. 30, 2018, an application claiming the benefit of Japanese Application No. 2017-149304, filed Aug. 1, 2017, the content of each of which is hereby incorporated by reference in its entirety.

TECHNICAL FIELD

The present invention relates to a patch.

BACKGROUND ART

Oxybutynin hydrochloride is known as one of anticholinergic agents, and it is known that the same is effective in treating overactive bladder with symptoms such as urinary urgency, or frequent urination. Overactive bladder exhibits a symptom of having micturition desire even when urine is not accumulated in the bladder due to contraction of bladder smooth muscle caused by activation of the acetylcholine nervous system for some reason. Oxybutynin can suppress the contraction of bladder smooth muscle owing to its anticholinergic effect to alleviate the symptom of overactive bladder.

As a formulation containing oxybutynin, an oral formulation has been heretofore known. When oxybutynin is administered orally, it is liable to be metabolized by the liver (first-pass effect) after being absorbed by the gastrointestinal tract to generate metabolites, such as N-desethyloxybutynin. It is known that these metabolites are more likely to cause side effects, such as thirst, constipation, and blurred vision, compared with oxybutynin itself.

With an oxybutynin-containing patch developed recently, oxybutynin is absorbed through the skin, and therefore the first-pass effect can be avoided so as to reduce the occurrence of the side effects (Refer to Patent Literature 1 to 4).

CITATION LIST

Patent Literature

[Patent Literature 1] WO 01/07018
[Patent Literature 2] WO 02/069942
[Patent Literature 3] WO 2004/019930
[Patent Literature 4] WO 2013/061969

SUMMARY OF INVENTION

Technical Problem

However, the present inventors have found that skin irritation cause by oxybutynin appears in some cases depending on the user's skin conditions or skin symptoms, when a patch containing oxybutynin is repeatedly used.

Under such circumstances, an object of the present invention is to provide a patch containing oxybutynin or a salt thereof, of which dermal irritancy due to oxybutynin is mitigated compared with the conventional patch.

Solution to Problem

As a result of detailed investigations, the present inventors have found that skin irritation by oxybutynin can be reduced by a patch containing a specific steroid, thereby completing the present invention.

Namely, the present invention provides the following [1] to [4].

[1] A patch comprising a backing, and an adhesive layer on the backing, wherein the adhesive layer contains at least one drug selected from the group consisting of oxybutynin and a pharmaceutically acceptable salt thereof, a pressure-sensitive adhesive base, and diflucortolone valerate, and the content of the diflucortolone valerate is 0.0007 to 0.05% by mass based on the total mass of the adhesive layer.

[2] The patch according to [1], wherein the mass ratio of the drug to the diflucortolone valerate is 180:1 to 20000:1.

[3] The patch according to [1] or [2], wherein the pressure-sensitive adhesive base contains at least one pressure-sensitive adhesive base selected from the group consisting of a rubber based pressure-sensitive adhesive base, and an acrylic pressure-sensitive adhesive base.

[4] A method for producing a patch comprising a backing, and an adhesive layer on the backing comprising:
a step of forming an adhesive layer by spreading an adhesive composition containing at least one drug selected from the group consisting of oxybutynin and a pharmaceutically acceptable salt thereof, a pressure-sensitive adhesive base, and diflucortolone valerate over a release liner, and
a step of laminating the backing on the thus formed adhesive layer; wherein
the content of the diflucortolone valerate is 0.0007 to 0.05% by mass based on the total mass of the adhesive layer.

Advantageous Effects of Invention

According to the present invention, without reducing the content of oxybutynin, a patch having reduced dermal irritancy of oxybutynin compared to the conventional patch may be provided. In addition, although skin atrophy tends to be observed when an external preparation containing a steroid is applied to the skin, skin atrophy is also unlikely observed when a patch of the present invention is applied.

DESCRIPTION OF EMBODIMENTS

The term "skin irritation" means herein a skin irritation to develop at an application site, when a patch containing oxybutynin or a pharmacologically acceptable salt thereof is applied to the skin, and includes specifically skin symptom, such as pruritus, erythema, eruption, pain, eczema, and dermatitis. In this regard, the presence or absence of skin irritation may be evaluated based on the scores given corresponding to the severity of erythema and edema as the criteria.

The term "skin atrophy" means herein a symptom in which, when a steroid is applied to the skin, the epidermis of the application site becomes thinner than the normal epidermis (the thickness of the epidermis in a state not affected by the steroid). For example, the presence or absence of skin atrophy may be judged by the criterion whether or not the thickness of the epidermis after an application of a patch to the skin is 50% or less as compared with the thickness of the normal epidermis.

A patch according to an Embodiment of the present invention is a patch comprising a backing, and an adhesive layer on the backing, wherein the adhesive layer contains at least one drug selected from the group consisting of oxybutynin and a pharmaceutically acceptable salt thereof, a pressure-sensitive adhesive base, and diflucortolone valerate.

The backing is a layer that physically supports the adhesive layer. There is no particular restriction on the material of the backing, insofar as it is generally used for a patch. Examples of the material of the backing include polyolefins such as polyethylene, polypropylene, and polybutadiene; polyesters such as poly(ethylene terephthalate), poly(butylene terephthalate) and poly(ethylene naphthalate); and synthetic resins such as an ethylene/vinyl acetate copolymer, a vinyl acetate/vinyl chloride copolymer, poly(vinyl chloride), polyamide, nylon, cellulose derivatives, and polyurethane. The form of the backing may be a film, a sheet, a sheet-like porous body, a sheet-like foamed body, a woven fabric, a knitted fabric, a nonwoven fabric, or a laminate thereof. Since a knitted fabric is excellent in elasticity, it is preferable from the viewpoint of fixation to the skin.

The adhesive layer contains at least one drug selected from the group consisting of oxybutynin and a pharmaceutically acceptable salt thereof, a pressure-sensitive adhesive base, and diflucortolone valerate.

The drug may be oxybutynin, pharmaceutically acceptable salts of oxybutynin, or a mixture thereof. Oxybutynin is also called 4-(diethylamino)-2-butynyl α-phenyl-cyclohexaneglycolate. Oxybutynin relaxes bladder smooth muscle by competitive inhibition of muscarinic receptors, thereby alleviating symptoms of overactive bladder, such as urinary urgency, or frequent urination.

A pharmaceutically acceptable salt of oxybutynin may be an inorganic acid salt, or an organic acid salt. Examples of an inorganic acid forming an inorganic acid salt of oxybutynin include hydrochloric acid, hydrobromic acid, silicic acid, and phosphoric acid. Examples of an organic acid forming an organic acid salt of oxybutynin include acetic acid, citric acid, fumaric acid, and maleic acid. Among them, oxybutynin hydrochloride, or oxybutynin acetate is preferred.

The content of oxybutynin or a pharmaceutically acceptable salt thereof may be an amount that can ensure an effective blood concentration of oxybutynin. The content of oxybutynin or a pharmaceutically acceptable salt thereof is, for example, in terms of the mass of oxybutynin and based on the total mass of the adhesive layer, preferably 4 to 50% by mass, more preferably 6 to 30% by mass, and further preferably 9 to 14% by mass. When the content of oxybutynin is 4% by mass or more, the amount of oxybutynin tends to become sufficient to reliably exert the pharmacological effect of oxybutynin. When the content of oxybutynin is 50% by mass or less, skin irritation by oxybutynin scarcely develops. When the mass of oxybutynin or a pharmaceutically acceptable salt thereof is reduced to the mass of oxybutynin, it may be calculated on the basis of the molecular weight.

There is no particular restriction on the pressure-sensitive adhesive base, insofar as it is used generally for a patch, and examples thereof include a rubber based pressure-sensitive adhesive base, an acrylic pressure-sensitive adhesive base, and a silicone based pressure-sensitive adhesive base. A preferable pressure-sensitive adhesive base is a rubber based pressure-sensitive adhesive base, or an acrylic pressure-sensitive adhesive base.

The rubber based pressure-sensitive adhesive base may be a polymer composed mainly of a natural or synthetic rubber, and examples thereof include polyisoprene, polyisobutylene, polybutadiene, a styrene/isoprene/styrene block copolymer (SIS block copolymer), a styrene/butadiene/styrene block copolymer, a styrene/butadiene rubber, and a styrene/isoprene rubber.

Examples of the acrylic pressure-sensitive adhesive base include a polymer of an alkyl (meth)acrylate, and a copolymer of an alkyl (meth)acrylate and a comonomer. In this regard, the alkyl (meth)acrylate means an alkyl acrylate, or an alkyl methacrylate. Examples of the alkyl (meth)acrylate include butyl (meth)acrylate, isobutyl (meth)acrylate, hexyl (meth)acrylate, octyl (meth)acrylate, 2-ethylhexyl (meth) acrylate, and decyl (meth)acrylate. The alkyl (meth)acrylates may be used singly or in combinations of two or more thereof. Examples of the comonomer include a hydroxyalkyl (meth)acrylate, ethylene, propylene, styrene, vinyl acetate, N-vinylpyrrolidone, and (meth)acrylic acid amide. These comonomers may be used singly or in combinations of two or more thereof. Specific examples of the acrylic pressure-sensitive adhesive base include copolymers containing at least two selected from butyl acrylate, 2-ethylhexyl acrylate, vinyl acetate, methacrylic acid, hydroxyethyl acrylate, glycidyl methacrylate, methoxyethyl acrylate, and acrylic acid; and more specifically DURO-TAK 87-2097, 87-2194, 87-2196, 87-2287, 87-2516 and 87-2852 (trade names, Henkel AG & Co.), as well as NISSETSU KP-77 and AS-370 (trade names, Nippon Carbide Industries Co., Inc.).

Examples of the silicone based pressure-sensitive adhesive base include organopolysiloxanes, such as dimethylpolysiloxanes, and condensation reaction products of a dimethylpolysiloxane and a silicate resin. Specific examples of the silicone based pressure-sensitive adhesive base include BIO-PSA X7-4201, BIO-PSA Q7-4501, 360Medical fluid 1000CS, and MDX 4-4210 (trade names, Dow Corning Corp.).

The content of the pressure-sensitive adhesive base is preferably 5 to 90% by mass, for example, based on the total mass of the adhesive layer, more preferably 10 to 50% by mass, and further preferably 10 to 30% by mass.

Diflucortolone valerate is also called 6α,9-difluoro-β-hydroxy-21-valeryloxy-16α-methyl-1,4-pregnadiene-3,20-dione. Diflucortolone valerate is a kind of steroid having a synthetic adrenocortical hormone effect, and has an anti-inflammatory effect similar to other steroids. According to Japanese atopic dermatitis clinical practice guideline 2016, diflucortolone valerate belongs to Class II (very strong) out of 5 classifications of steroids.

The content of diflucortolone valerate is preferably 0.0007 to 0.05% by mass based on the total mass of the adhesive layer, more preferably 0.0009 to 0.03% by mass, and further preferably 0.001 to 0.01% by mass. When the content of diflucortolone valerate is 0.0007% by mass or more, it tends to become easier to alleviate skin irritation of oxybutynin. When the content of diflucortolone valerate is 0.05% by mass or less, skin atrophy at an application site becomes less likely to occur.

The mass ratio of oxybutynin to diflucortolone valerate contained in the adhesive layer may be 150:1 to 25000:1, preferably 180:1 to 20000:1, more preferably 300:1 to 140000:9 (that is, 15555:1), and particularly preferably 900:1 to 14000:1. When the adhesive layer contains a pharmaceutically acceptable salt of oxybutynin as the drug, the mass of the pharmaceutically acceptable salt of oxybutynin is reduced by calculation to the mass of oxybutynin. When the mass ratio of oxybutynin to diflucortolone valerate is not more than 25000:1 (that is, the mass of oxybutynin is not more than 25000 times the mass of diflucortolone valerate), skin irritation by oxybutynin can be more effectively alleviated.

The adhesive layer may additionally contain another component (such as a tackifier, a plasticizer, a filler, a stabilizer, a drug penetration enhancer, a perfume, and a coloring agent).

Examples of the tackifier include a terpene resin, a terpene phenol resin, a rosin ester resin, a hydrogenated rosin ester resin, an alicyclic saturated hydrocarbon resin, and a petroleum resin. The terpene resin is preferably a hydrogenated terpene resin. Examples of the terpene resin include an α-pinene resin, a β-pinene resin, an aromatic modified terpene resin, and a terpene phenol resin.

Examples of the plasticizer include paraffin oil (such as liquid paraffin), squalane, squalene, vegetable oils (such as olive oil, camellia oil, castor oil, tall oil, peanut oil, spearmint oil, eucalyptus oil, jojoba oil, white camphor oil, sunflower oil, and orange oil), fats and oils (such as dibutyl phthalate, and dioctyl phthalate), and liquid rubber (such as liquid polybutene, and liquid isoprene rubber).

Examples of the filler include powders of a metal compound (such as aluminum oxide, aluminum hydroxide, zinc oxide, titanium oxide, and calcium carbonate), ceramics (such as talc, clay, kaolin, silica, hydroxyapatite, synthetic aluminum silicate, and magnesium aluminometasilicate), or an organic compound (such as cellulose powder, and stearates), and short fibers of a resin containing the above.

As the penetration enhancer any compound heretofore known to have a penetration enhancing effect in the skin may be used. Examples of the penetration enhancer include organic acids and salts thereof (such as aliphatic carboxylic acids having 6 to 20 carbon atoms (hereinafter also referred to as "fatty acids") and salts thereof, as well as cinnamic acid and salts thereof), organic acid esters (such as fatty acid esters, and cinnamic acid esters), organic acid amides (such as fatty acid amides), fatty alcohols, polyhydric alcohols, ethers (such as fatty ethers, and polyoxyethylene alkyl ethers). These absorption enhancers may have an unsaturated bond, and may have a cyclic, linear, or branched chemical structure. The penetration enhancer may also be a monoterpene compound, a sesquiterpene compound, or a vegetable oil (such as olive oil). The penetration enhancers may be used singly, or in combinations of two or more thereof.

Examples of the organic acid include aliphatic (mono, di, or tri) carboxylic acids (such as acetic acid, propionic acid, citric acid (including anhydrous citric acid), isobutyric acid, caproic acid, caprylic acid, fatty acids, lactic acid, maleic acid, pyruvic acid, oxalic acid, succinic acid, and tartaric acid), aromatic carboxylic acids (such as phthalic acid, salicylic acid, benzoic acid, and acetylsalicylic acid), cinnamic acid, alkanesulfonic acids (such as methanesulfonic acid, ethanesulfonic acid, propanesulfonic acid, and butanesulfonic acid), alkylsulfonic acid derivatives (such as a polyoxyethylene alkyl ether sulfonic acid, N-2-hydroxyethylpiperazine-N'-2-ethanesulfonic acid), cholic acid derivatives (such as dehydrocholic acid). These organic acids may be alkali metal salts such as sodium salts. Among them, aliphatic carboxylic acids, aromatic carboxylic acids, or salts thereof are preferable, and acetic acid, sodium acetate, or citric acid is particularly preferable.

Examples of the fatty acid include lauric acid, myristic acid, palmitic acid, stearic acid, isostearic acid, oleic acid, linoleic acid, and linolenic acid.

Examples of the organic acid ester include ethyl acetate, propyl acetate, cetyl lactate, lauryl lactate, methyl salicylate, ethylene glycol salicylate, methyl cinnamate, and fatty acid esters. Examples of the fatty acid ester include methyl laurate, hexyl laurate, isopropyl myristate, myristyl myristate, octyldodecyl myristate, and cetyl palmitate. The fatty acid ester may be also glycerol fatty acid ester, propylene glycol fatty acid ester, sorbitan fatty acid ester, polyethylene glycol sorbitan fatty acid ester, polyethylene glycol fatty acid ester, sucrose fatty acid ester, or polyoxyethylene hydrogenated castor oil. Specific examples of the fatty acid ester include glycerol monocaprylate, glycerol monocaprate, glycerol monolaurate, glycerol monooleate, sorbitan monolaurate, sucrose monolaurate, Polysorbate 20 (trade name), propylene glycol monolaurate, polyethylene glycol monolaurate, polyethylene glycol monostearate, Span 20, Span 40, Span 60, Span 80, Span 120 (trade names), Tween 20, Tween 21, Tween 40, Tween 60, Tween 80 (trade names), and NIKKOL HCO-60 (trade name).

Examples of the organic acid amide include fatty acid amides (such as lauric acid diethanolamide), hexahydro-1-dodecyl-2H-azepin-2-one (also called Azone) and its derivatives, and pyrrothiodecane.

Fatty alcohol means an aliphatic alcohol having 6 to 20 carbon atoms. Examples of the fatty alcohol include lauryl alcohol, myristyl alcohol, oleyl alcohol, isostearyl alcohol, and cetyl alcohol. Examples of the polyhydric alcohol include propylene glycol.

Examples of the polyoxyethylene alkyl ether include polyoxyethylene lauryl ether.

Examples of the monoterpene compound include geraniol, thymol, eugenol, terpineol, 1-menthol, borneol, d-limonene, isoeugenol, isoborneol, nerol, and dl-camphor.

More preferable is oleyl alcohol, lauryl alcohol, isostearyl alcohol, lauric acid diethanolamide, glycerol monocaprylate, glycerol monocaprate, glycerol monooleate, sorbitan monolaurate, propylene glycol monolaurate, polyoxyethylene lauryl ether, or pyrrothiodecane. Fatty acids are preferred, and oleic acid is particularly preferable.

The adhesive layer may be provided with a release liner on the side which is opposite to the backing and comes into contact with the skin. The release liner is a liner to be removed when the patch is used, and is not particularly restricted insofar as it is generally used for a patch. Examples of the material for the release liner include polyester (such as poly(ethylene terephthalate) (PET)), polyolefin (such as polypropylene, and polyethylene), cellulose compounds (such as paper). The release liner may be in the form of a sheet consisting of a laminate of the above materials. It is preferable that the surface of the release liner is release-treated with a silicone, a fluorinated polyolefin, or the like.

The patch according to this Embodiment can be produced, for example, by the following method.

1) The ingredients of an adhesive layer are weighed out, then, according to need, heating and addition of a solvent are performed, and the mixture is mixed to be homogenized.

2) The obtained adhesive composition is applied to the release surface of a release liner at a constant thickness, and, if necessary, dried to remove the solvent component to form an adhesive layer.

3) The backing is layered on the adhesive layer.

4) The laminate is cut into a predetermined shape (for example, a rectangle having a short side of 3 cm to 14 cm, and a long side of 7 cm to 20 cm, or a circle having a diameter of 1 cm to 10 cm).

EXAMPLES

The patch of the present invention will be described below in more detail using Examples and Comparative Examples.

Test Example 1

Evaluations of Skin Irritation and Skin Atrophy

Each patch of Example 1 and Comparative Examples 1 to 8 was prepared in accordance with the descriptions of Table 1 or 2. In Tables 1 and 2, the numerical values are expressed in % by mass, unless otherwise specified.

HWY: Slc rats (6 to 7 week-old, female) were purchased and acclimated for not less than 6 days. During the acclimation period, the hairs on the back of the rat were clipped and shaved. Rats in good general condition and skin condition were selected from all the rats, and grouping was performed to form groups consisting of even body weight rats. Any one of the patches and the patch of Comparative Example 1 as the control were applied to each group of rats. Specifically, on the day of application, an application site (about 1.5 cm×1.5 cm) was set on the skin of the rat back (shaved region) and its four corners were marked. The patches obtained above were applied on to the marked application sites, respectively. After application, a mesh adhesive bandage was bonded so as to cover the application site, which was further covered with a lint cloth, and fixed with an adhesive elastic bandage. The lint cloth, adhesive bandage and patch were peeled off 24 hours after the application, and the severity of skin irritation was evaluated with respect to the rats in each group. After the evaluation of the severity of skin irritation, the skin at the application site was excised to prepare a skin section sample, and the severity of skin atrophy was evaluated.

The evaluation of skin irritation was carried out based on the severity criteria of Draize, et al. (reference: Draize JH, et al., J. Pharmacol. Exp. Ther., 1944: 82: 377-390) 0.5 hour after removal of the patch. Specifically, by observing the skin of the application site after 0.5 hour from peeling, scores were given with respect to (1) erythema and eschar formation, and (2) edema formation according to the following criteria, and the average value was calculated for each group. Then a relative value of the average score of an Example with respect to the average score of the corresponding Comparative Example was calculated.

<Severity Criteria of Draize, et al.>
(1) Erythema and Eschar Formation
  0: No erythema
  1: Very slight erythema (barely perceptible)
  2: Well-defined erythema
  3: Moderate to severe erythema
  4: Severe erythema (beet redness) to slight eschar formation (injuries at depth)
(2) Edema Formation
  0: No edema
  1: Very slight edema (barely perceptible)
  2: Slight edema (edges of area well defined by definite raising)
  3: Moderate edema (raised approximately about 1 mm)
  4: Severe edema (raised more than 1 mm and extending beyond area of exposure)

The evaluation of skin atrophy was performed on rats (2 animals in each group) having undergone the evaluation of skin irritation. Whole blood was collected from the abdominal aorta of each animal under anesthesia by inhalation of isoflurane. After blood collection, a section of epidermis of the skin including each application site was sampled, and the obtained epidermis section was fixed with a 10% formalin solution. The central portion of the application site of the epidermis section after fixation was cut out, embedded in paraffin, and stained with hematoxylin and eosin (HE staining), and the obtained sample was observed with a microscope (trade name: BX50, manufactured by Olympus Corporation). An image of the sample photographed with a microscope was analyzed using an image analysis software (trade name: WinROOF ver. 7.3, produced by Mitani Corporation), and the thickness of the epidermis was measured. For each epidermis section, the thickness of the epidermis was measured at five positions, and the average value was calculated. In a case where the thickness of the epidermis in the application site exceeded 50% of the thickness of the epidermis at the site without application (normal skin), it was rated as "A", and in a case where the same is 50% or less, it was rated as "B".

TABLE 1

|  | Comp. Ex. 1 | Ex. 1 | Comp. Ex. 2 | Comp. Ex. 3 | Comp. Ex. 4 | Comp. Ex. 5 |
| --- | --- | --- | --- | --- | --- | --- |
| Oxybutynin hydrochloride | 15 | 15 | 15 | 15 | 15 | 15 |
| SIS block copolymer | 17.2 | 17.17 | 17.17 | 17.17 | 17.17 | 17.17 |
| Acrylic acid ester copolymer | 1.9 | 1.91 | 1.91 | 1.91 | 1.91 | 1.91 |
| Alicyclic saturated hydrocarbon resin | 40.1 | 40.06 | 40.06 | 40.06 | 40.06 | 40.06 |
| Liquid paraffin | 14.3 | 14.31 | 14.31 | 14.31 | 14.31 | 14.31 |
| Sodium acetate | 9 | 9 | 9 | 9 | 9 | 9 |
| Diflucortolone valerate | — | 0.05 | — | — | — | — |
| Clobetasol propionate | — | — | 0.05 | — | — | — |
| Amcinonide | — | — | — | 0.05 | — | — |
| Mometasone furancarboxylate | — | — | — | — | 0.05 | — |
| Fluocinonide | — | — | — | — | — | 0.05 |
| Other ingredients | 2.5 | 2.5 | 2.5 | 2.5 | 2.5 | 2.5 |
| Skin irritation | 1 | 0 | 0 | 0 | 0 | 0 |
| Skin atrophy | A | A | B | B | B | B |

TABLE 2

|  | Comp. Ex. 6 | Comp. Ex. 7 | Comp. Ex. 8 |
|---|---|---|---|
| Oxybutynin hydrochloride | 15 | 15 | 15 |
| SIS block copolymer | 17.17 | 17.17 | 17.17 |
| Acrylic acid ester copolymer | 1.91 | 1.91 | 1.91 |
| Alicyclic saturated hydrocarbon resin | 40.06 | 40.06 | 40.06 |
| Liquid paraffin | 14.31 | 14.31 | 14.31 |
| Sodium acetate | 9 | 9 | 9 |
| Dexamethasone propionate | 0.05 | — | — |
| Beclomethasone propionate | — | 0.05 | — |
| Fluocinolone acetonide | — | — | 0.05 |
| Other ingredients | 2.5 | 2.5 | 2.5 |
| Skin irritation | 0 | 1 | 0 |
| Skin atrophy | B | A | B |

The severity of skin irritation of any of Example 1 and Comparative Examples 2 to 8 is a relative value with respect to the average score of Comparative Example 1. Among the patches containing diflucortolone valerate, clobetasol propionate, amcinonide, mometasone furancarboxylate, fluocinonide, dexamethasone propionate, beclomethasone propionate, or fluocinolone acetonide, only the patch containing diflucortolone valerate (Example 1) alleviated skin irritation due to oxybutynin hydrochloride, and did not cause skin atrophy.

In Japan, according to Japanese atopic dermatitis clinical practice guideline 2016, steroids for external use are classified into five classes (class I: Strongest, class II: Very strong, class III: Strong, class IV: Mild, and class V: Weak) based on their anti-inflammatory effect and vasoconstriction effect. Referring to Tables 1 and 2, the patch of Example 1 containing diflucortolone valerate (class II) alleviated skin irritation due to oxybutynin, and did not cause skin atrophy. In contrast, the patches of Comparative Examples 3 to 5 containing amcinonide (class II), mometasone furancarboxylate (class II), or fluocinonide (class II) caused skin atrophy, although they could alleviate skin irritation due to oxybutynin.

Test Example 2

Concentration of Diflucortolone Valerate

Each patch of Examples 1 to 5 and Comparative Examples 9 and 10 was prepared in accordance with the descriptions of Table 3. In Table 3, the numerical values are expressed in % by mass, unless otherwise specified.

HWY: Slc rats (6 to 7 week-old, female) were purchased and acclimated for not less than 6 days. During the acclimation period, the hairs on the back of the rats were clipped and shaved. Rats in good general condition and skin condition were selected from all the rats, and grouping was performed to form groups consisting of even body weight rats. Any one of the patches and the patch of Comparative Example 1 as the control were applied to each group of rats. More specifically, the obtained patch was applied to the back of the rat for 24 hours, and then the patch was peeled off. Thereafter, the severities of skin irritation and skin atrophy in each group of rats were evaluated in the same manner as in Test Example 1. The severity of skin irritation of any of Examples 1 to 5 and Comparative Examples 9 and 10 is a relative value with respect to the average score of Comparative Example 1.

TABLE 3

|  | Comp. Ex. 9 | Ex. 1 | Ex. 2 | Ex. 3 |
|---|---|---|---|---|
| Oxybutynin hydrochloride | 15 | 15 | 15 | 15 |
| SIS block copolymer | 17.2 | 17.17 | 17.18 | 17.18 |
| Acrylic acid ester copolymer | 1.9 | 1.91 | 1.91 | 1.91 |
| Alicyclic saturated hydrocarbon resin | 40 | 40.06 | 40.08 | 40.085 |
| Liquid paraffin | 14.3 | 14.31 | 14.32 | 14.32 |
| Sodium acetate | 9 | 9 | 9 | 9 |
| Diflucortolone valerate | 0.1 | 0.05 | 0.01 | 0.005 |
| Other ingredients | 2.5 | 2.5 | 2.5 | 2.5 |
| Skin irritation | 0 | 0 | 0 | 0 |
| Skin atrophy | B | A | A | A |

|  | Ex. 4 | Ex. 5 | Comp. Ex. 10 |
|---|---|---|---|
| Oxybutynin hydrochloride | 15 | 15 | 15 |
| SIS block copolymer | 17.18 | 17.18 | 17.18 |
| Acrylic acid ester copolymer | 1.91 | 1.91 | 1.91 |
| Alicyclic saturated hydrocarbon resin | 40.0891 | 40.0893 | 40.0895 |
| Liquid paraffin | 14.32 | 14.32 | 14.32 |
| Sodium acetate | 9 | 9 | 9 |
| Diflucortolone valerate | 0.0009 | 0.0007 | 0.0005 |
| Other ingredients | 2.5 | 2.5 | 2.5 |
| Skin irritation | 0 | 0.4 | 0.8 |
| Skin atrophy | A | A | A |

Test Example 3

Skin Permeability of Oxybutynin

The time course of the skin permeation amount of oxybutynin was measured using hairless mice (7 week-old, male) with respect to the patches of Examples 1 and 6, and Comparative Example 1. On the excised skin of the hairless mouse, 3 pieces of each patch were bonded. The skin was set in a vertical flow-through type cell, which was then filled with physiological saline, and connected with a roller pump and a fraction collector by means of a tube. Next, the circulating phase of the cell was connected with a thermostatic circulation tank set at 32° C. by means of a tube, and the receiver liquid was collected every 4 hours with stirring using a magnetic stirrer. The test was repeated 6 times for each patch. The results of the average cumulative skin permeation amount of oxybutynin for the respective patches are shown in Table 4.

TABLE 4

|  | Comp. Ex. 1 | Ex. 1 | Ex. 6 |
|---|---|---|---|
| Oxybutynin hydrochloride | 15 | 15 | 15 |
| SIS block copolymer | 17.2 | 17.17 | 17.18 |
| Acrylic acid ester copolymer | 1.9 | 1.91 | 1.91 |
| Alicyclic saturated hydrocarbon resin | 40.1 | 40.06 | 40.089 |
| Liquid paraffin | 14.3 | 14.31 | 14.32 |
| Sodium acetate | 9 | 9 | 9 |
| Diflucortolone valerate | 0 | 0.05 | 0.001 |
| Other ingredients | 2.5 | 2.5 | 2.5 |
| Average cumulative skin permeation amount [$\mu g/cm^2/24$ hr] | 464.2 | 475.7 | 463.9 |

The cumulative skin permeation amount of oxybutynin from the bonding up to 24 hours thereafter was measured and the average value of the two animals was calculated. Among the patches of Examples 1, 6 and Comparative Example 1, there was no significant difference in the cumulative skin permeation amounts of oxybutynin for 24 hours from the application. Therefore, it was revealed that skin irritation was not alleviated due to the decrease of the skin permeation amount of oxybutynin.

Test Example 4

Stability of Diflucortolone Valerate

The patch of Example 3 was stored at 40° C. for 1 month, or 6 months in accordance with the description of the Japanese Pharmacopoeia, and thereafter the content of diflucortolone valerate contained in the adhesive layer was measured by high performance liquid chromatography. The relative contents of diflucortolone valerate in the patches after storage under the respective conditions with respect to the content of diflucortolone valerate in the patch at the time of preparation (initial value) were calculated, and shown in Table 5.

TABLE 5

| Storage conditions | Example 3 |
|---|---|
| Initial value | 100 |
| 40° C. for 1 month | 104.1 |
| 40° C. for 6 months | 101.8 |

Test Example 5

Evaluation of Skin Irritation and Skin Atrophy

In the same manner as in Test Example 1, each of patches of Example 7 and Comparative Examples 11 to 13 was prepared, and their skin irritation and skin atrophy were evaluated. In Table 6, the numerical values are expressed in % by mass, unless otherwise specified.

TABLE 6

|  | Ex. 7 | Comp. Ex. 11 | Comp. Ex. 12 | Comp. Ex. 13 |
|---|---|---|---|---|
| Oxybutynin hydrochloride | 15 | 15 | 15 | 15 |
| SIS block copolymer | 17.18 | 17.18 | 17.18 | 17.18 |
| Acrylic acid ester copolymer | 1.91 | 1.91 | 1.91 | 1.91 |
| Alicyclic saturated hydrocarbon resin | 40.07 | 40.07 | 40.07 | 40.07 |
| Liquid paraffin | 14.32 | 14.32 | 14.32 | 14.32 |
| Sodium acetate | 9 | 9 | 9 | 9 |
| Diflucortolone valerate | 0.02 | — | — | — |
| Amcinonide | — | 0.02 | — | — |
| Mometasone furancarboxylate | — | — | 0.02 | — |
| Fluocinonide | — | — | — | 0.02 |
| Other ingredients | 2.5 | 2.5 | 2.5 | 2.5 |
| Skin irritation | 0 | 0 | 0 | 0 |
| Skin atrophy | A | B | B | B |

The severity of skin irritation of any of Example 7 and Comparative Examples 11 to 13 is a relative value with respect to the average score of Comparative Example 1. The patch of Example 7 not only alleviated skin irritation due to oxybutynin hydrochloride, but also did not cause skin atrophy.

Test Example 6

Evaluation of Skin Irritation

The patches of Comparative Example 14, and Examples 8 and 9 were prepared according to the descriptions in Table 7, and the skin irritation was evaluated in the same manner as in Test Example 1. In Table 7, the numerical values are expressed in % by mass, unless otherwise specified. The severity of skin irritation of either of Examples 8 and 9 is a relative value with respect to the average score of Comparative Example 14.

TABLE 7

|  | Comp. Ex. 14 | Ex. 8 | Ex. 9 |
|---|---|---|---|
| Oxybutynin hydrochloride | 11.25 | 11.25 | 11.25 |
| SIS block copolymer | 11.41 | 11.41 | 11.40 |
| Polyisobutylene | 4.89 | 4.89 | 4.89 |
| Acrylic acid ester copolymer | 4.08 | 4.08 | 4.08 |
| Alicyclic saturated hydrocarbon resin | 42.79 | 42.785 | 42.76 |
| Liquid paraffin | 15.28 | 15.28 | 15.27 |
| Sodium acetate | 5.3 | 5.3 | 5.3 |
| Diflucortolone valerate | 0 | 0.005 | 0.05 |
| Other ingredients | 5 | 5 | 5 |
| Skin irritation | 1 | 0 | 0 |

Test Example 7

Evaluation of Skin Irritation (Consecutive Administrations)

The patches of Comparative Example 15, and Example 10 were prepared according to the descriptions in Table 8. In Table 8, the numerical values are expressed in % by mass, unless otherwise specified. Skin irritation was evaluated when any of the patches of Examples 3, 8, and 10, and Comparative Examples 1, 14, and 15 was administered consecutively twice. Specifically, an application site (about 1.5 cm×1.5 cm) was set on the skin of the rat back (shaved region) and its four corners were marked. The rats were divided into the group to be applied with the patch of Comparative Example, and the group to be applied with the patch of Example, such that the number of rats in each group was 6 to 8. The patches obtained above were applied on to the marked application sites, respectively (first administration). After application, a mesh adhesive bandage was bonded so as to cover the application site, which was further covered with a lint cloth followed by fixation with an adhesive elastic bandage. The lint cloth, adhesive bandage and patch were peeled off 24 hours after the application. The second patch was applied to the same site 0.5 hour after the peeling (second administration). Keeping the second patch in the application site for 24 hours, then it was peeled off, and after another 0.5 hour the skin irritation was evaluated in the same manner as in Test Example 1.

TABLE 8

|  | Comp. Ex. 15 | Ex. 10 |
|---|---|---|
| Oxybutynin hydrochloride | 10 | 10 |
| SIS block copolymer | 11.59 | 11.59 |
| Polyisobutylene | 4.97 | 4.97 |
| Acrylic acid ester copolymer | 4.14 | 4.14 |
| Alicyclic saturated hydrocarbon resin | 43.47 | 43.465 |
| Liquid paraffin | 15.53 | 15.53 |
| Sodium acetate | 5.3 | 5.3 |
| Diflucortolone valerate | 0 | 0.005 |
| Other ingredients | 5 | 5 |

The results are shown in Table 9. The severities of skin irritation of Examples 3, 8, and 10 are relative values respectively with respect to the average scores of Comparative Examples 1, 14, and 15. The severities of skin irritation of the patches of the Examples were lower than those of the patches of the Comparative Examples.

TABLE 9

|  | Comp. Ex. 1 | Ex. 3 | Comp. Ex. 14 | Ex. 8 | Comp. Ex. 15 | Ex. 10 |
|---|---|---|---|---|---|---|
| Skin irritation | 1 | 0.3 | 1 | 0 | 1 | 0 |

The invention claimed is:

1. A patch comprising a backing, and an adhesive layer on the backing, wherein:
   the adhesive layer contains at least one drug selected from the group consisting of oxybutynin and a pharmaceutically acceptable salt thereof, a pressure-sensitive adhesive base, and diflucortolone valerate, and
   the content of the diflucortolone valerate is 0.0007 to 0.05% by mass based on the total mass of the adhesive layer; and
   wherein skin irritation of the oxybutynin and a pharmaceutically acceptable salt thereof is reduced; and
   wherein the mass ratio of the oxybutynin to the diflucortolone valerate is 180:1 to 20000:1.

2. The patch according to claim 1, wherein the pressure-sensitive adhesive base comprises at least one selected from the group consisting of a rubber based pressure-sensitive adhesive base and an acrylic pressure-sensitive adhesive base.

3. The patch according to claim 1, wherein the pressure-sensitive adhesive base comprises at least one selected from the group consisting of a rubber based pressure-sensitive adhesive base and an acrylic pressure-sensitive adhesive base.

* * * * *